(12) United States Patent
Chou et al.

(10) Patent No.: US 6,531,701 B2
(45) Date of Patent: Mar. 11, 2003

(54) REMOTE TRACE GAS DETECTION AND ANALYSIS

(75) Inventors: Mau-Song Chou, Rancho Palos Verdes, CA (US); John C. Brock, Redondo Beach, CA (US)

(73) Assignee: TRW Inc., Redondo Beach, CA (US)

( * ) Notice: Subject to any disclaimer, the term of this patent is extended or adjusted under 35 U.S.C. 154(b) by 23 days.

(21) Appl. No.: 09/808,489

(22) Filed: Mar. 14, 2001

(65) Prior Publication Data

US 2002/0166969 A1 Nov. 14, 2002

(51) Int. Cl.$^7$ ................................................ G01N 21/35

(52) U.S. Cl. .............................. 250/339.08; 250/341.6

(58) Field of Search ......................... 250/339.08, 341.6, 250/338.5, 372

(56) References Cited

U.S. PATENT DOCUMENTS 4,060,327 A * 11/1977 Jacobowitz et al. ........ 356/328
4,496,839 A * 1/1985 Bernstein et al. ........ 250/341.6

OTHER PUBLICATIONS

Stephen L. Dieckman et al. "Millimiter–Wave Measurements of Molecular Spectra with Application to Environmental Monitoring", IEEE Transactions on Instrumentation and Measurement, vol. 45, No. 1, Feb. 1996 pp. 225–320.

* cited by examiner

Primary Examiner—Constantine Hannaher
Assistant Examiner—Shun Lee
(74) Attorney, Agent, or Firm—Harness, Dickey & Pierce, P.L.C.

(57) ABSTRACT

A system for the remote detection and analysis of trace chemical agents in the air. A beam of electromagnetic radiation is used to radiate a cloud. The radiation energy that is absorbed by the cloud is thermalized by collisional energy transfer between the molecules that absorb the radiation. Increases in the cloud temperature increase the emission intensity of the molecules against the background, resulting in improved detection of the target molecules. A tracking telescope is used to collect the thermal emissions generated by the radiation beam. A spectrometer is used to resolve the emissions from the cloud and generate an emissions spectrum. The wavelength of the electromagnetic radiation can be selected to be in resonance with the absorption lines of water or oxygen molecules in the cloud, or to be in resonance with absorption lines of known target molecules in the cloud to generate the heat.

18 Claims, 5 Drawing Sheets

Fig. 1

Fig. 2(a) Sarin

Fig. 2(b) Soman

Fig. 2(c) Tabun

REMOTE TRACE GAS DETECTION AND ANALYSIS

BACKGROUND OF THE INVENTION

1. Field of the Invention

This invention relates generally to a method for detecting trace gases in the air and, more particularly, to a method of radiating a chemical cloud to heat the cloud and increase its temperature relative to the background, and then detecting chemicals in the cloud by spectroscopy.

2. Discussion of the Related Art

It is known in the art to detect certain constituents in a chemical cloud in the air by spectral analysis of the molecules making up the cloud. This type of chemical detection has many applications, including detecting natural gas leaks from underground pipes, chemical clouds from chemical spills, volatile organic vapor (VOC) from chemical processes, pollution from smoke stacks and the like, military chemical warfare agents, and other toxic gases present in the air. Typically, this type of spectral analysis of a chemical cloud is performed remotely, sometimes up to 10–20 km away, because the constituents in the cloud may be toxic, and thus a threat to health, or it may not be possible to directly detect the chemical cloud. The distance the detecting instrument has to be from the cloud for this remote type of passive sensing depends on the particular application, and different systems exist for different applications.

To perform this type of detection and analysis, a spectrometer, such as a Fourier transform infrared (FTIR) spectrometer, is directed towards the chemical agent cloud from a remote location, so that it passively receives emissions therefrom. If the chemical cloud is warmer than the background, such as sky, mountains, or other terrain, along the field-of-view of the spectrometer, target molecules in the cloud will exhibit emissions having an energy greater than the background emissions from the sky. If the chemical cloud is the same temperature as the sky, the target molecules within the cloud are absorbing photons at the same rate that they are emitting photons, so that there is no net energy exchange between the cloud and the background, and no difference relative to the background. As the temperature of the cloud increases, more photons are released from the chemicals in the cloud, which are available to be received by the spectrometer.

The spectral display generated by the spectrometer from the emissions provides emission lines and bands at certain wavelengths that is indicative of the atoms and molecules in the cloud. Because each material has its own spectral "fingerprint" representative of its molecules, the detected spectral display can be compared to a known "fingerprint" of a particular chemical to determine if that chemical exists in the cloud.

A problem exists with the passive remote sensing techniques that are currently used in the art because the temperature difference between the chemical cloud and the sky is often very small. In many cases, the temperature of the cloud is only about 2–3° C. warmer than the temperature of the background. Because of such a small temperature difference, the detectable emissions from the cloud is typically very weak. This results in a poor signal-to-noise ratio, and thus poor detection sensitivity and possibly a high false alarm rate.

What is needed is a remote chemical detection system that causes the chemical cloud to be heated so that the temperature of the cloud is significantly different than the background. It is therefore an object of the present invention to provide a remote chemical detection system of this type.

SUMMARY OF THE INVENTION

In accordance with the teachings of the present invention, a technique for the remote detection and analysis of trace chemicals in the air is disclosed. A beam of electromagnetic radiation from an electromagnetic radiation source is used to radiate a suspected chemical cloud. The radiation energy that is absorbed by the cloud is quickly thermalized due to a rapid collision energy transfer between the molecules that absorb the radiation and the surrounding air molecules. This collisional energy redistribution will result in heating the chemicals in the cloud. An increase in the temperature of the cloud will increase the emission intensity of the molecules against the background, resulting in an improvement in the detection of the chemicals.

A tracking telescope is then used to collect the thermal emissions of the target molecules generated by the radiation. The tracking telescope can be located in the vicinity of the electromagnetic radiation source such that the viewing axis of the telescope is preferably coaxial with the propagation direction of the electromagnetic radiation. A spectrometer, such as an FTIR spectrometer, is used to resolve the emissions from the cloud that are enhanced by the radiation and to generate an emissions spectrum. The emissions spectrum is used to identify suspect molecules in the cloud by comparing the detected emissions to the known "fingerprint" vibrational spectrum of the suspect molecules.

The electromagnetic radiation source, telescope and FTIR spectrometer can be housed on a platform to scan over a wide area for surveillance of chemical clouds. Alternatively, the tracking telescope and the FTIR spectrometer can be located at a separate location from that of the electromagnetic radiation source. The viewing axis of the telescope will intersect with the beam of the electromagnetic beam. In this arrangement the location of the chemical cloud can be determined based on the intersection of the electromagnetic radiation beam and the view axis of the telescope.

The electromagnetic radiation can be microwave, millimeter wave, infrared, visible, or ultraviolet radiation. The wavelength of the electromagnetic radiation can be selected to be in resonance with the absorption lines of the chemicals, or of water vapor or oxygen molecules that are commonly present in the cloud. If the wavelength of the electromagnetic radiation is chosen to be in resonance with the absorption lines of the target chemical molecules, the returned emission intensity, as a function of the excitation wavelength, can be used to provide an increased discrimination of the chemicals against possible interference background chemicals.

Additional objects, features and advantages of the present invention will become apparent from the following description and appended claims taken in conjunction with the accompanying drawings.

BRIEF DESCRIPTION OF THE DRAWINGS

FIG. 1 is a plan view of a remote spectral analysis sensing system, according to a preferred embodiment of the present invention;

FIGS. 2(*a*)–2(*d*) show the spectral footprint of four different chemical agents; and FIG. 3 is a graph with wavelength on the horizontal axis and the absorption of the agent VX and output intensity of a $CO_2$ laser on the vertical axis showing the overlapping of a $CO_2$ laser with absorption spectrum of the agent VX.

DETAILED DESCRIPTION OF THE PREFERRED EMBODIMENTS

The following discussion of the preferred embodiments directed to a technique for the remote sensing of a chemical cloud is merely exemplary in nature, and is in no way intended to limit the invention or its applications or uses.

Figure 1:
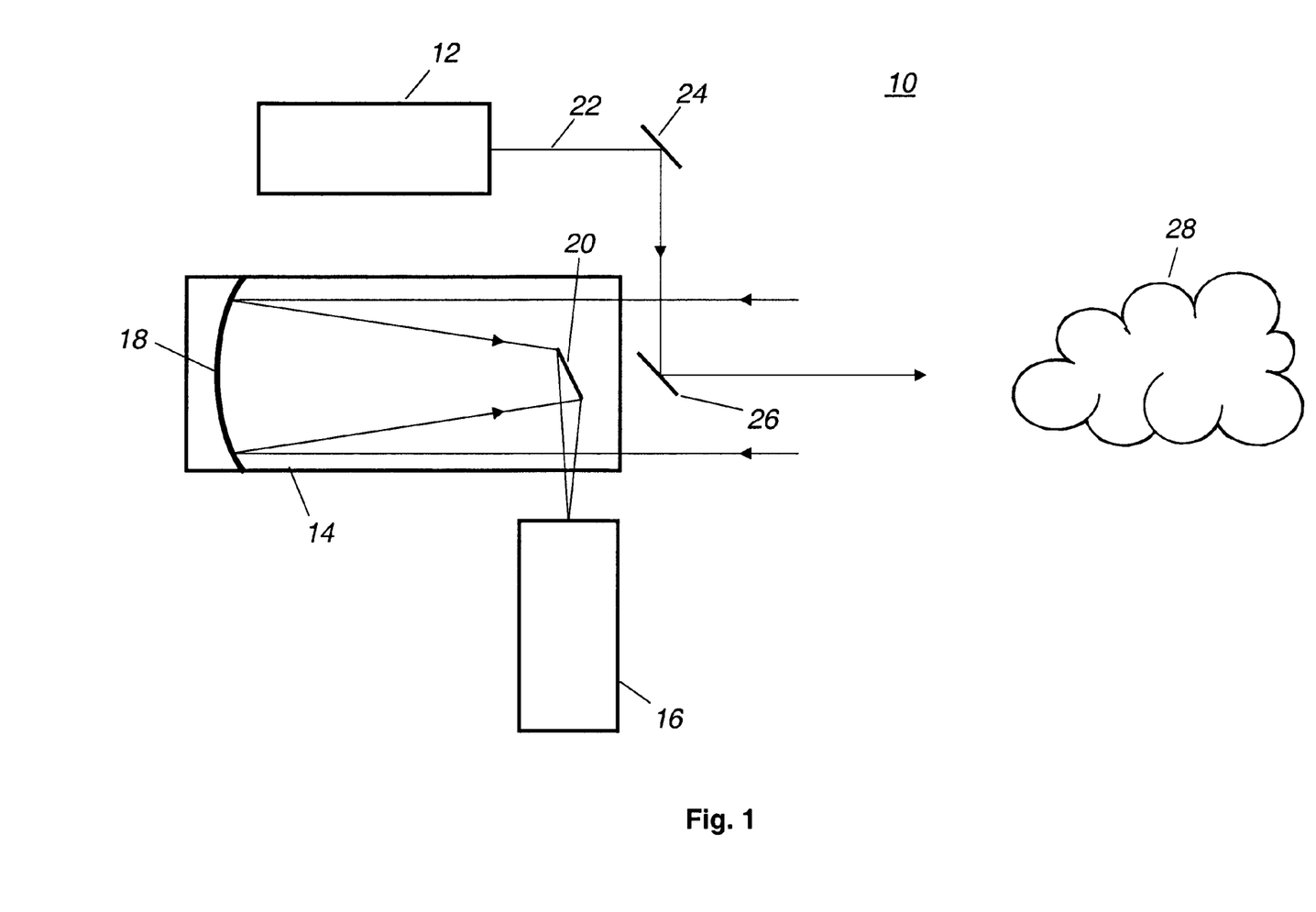
Figure 2A:
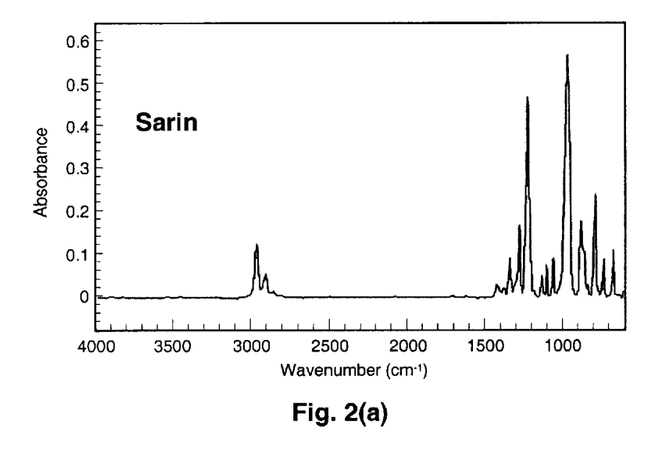
Figure 2B:
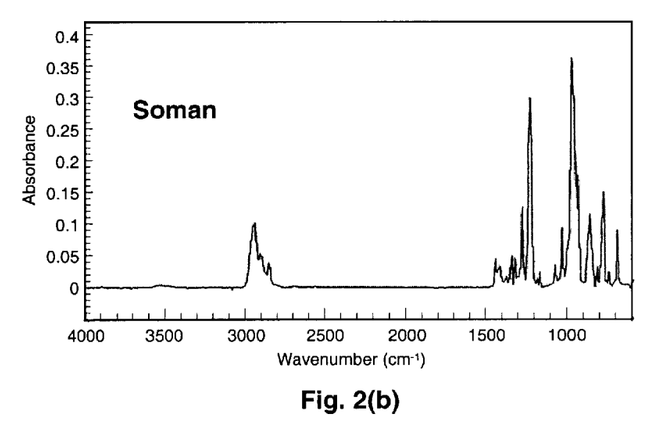
Figure 2C:
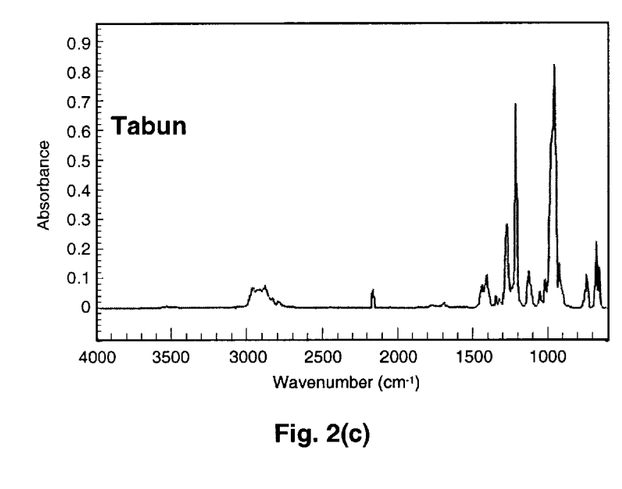
Figure 2D:
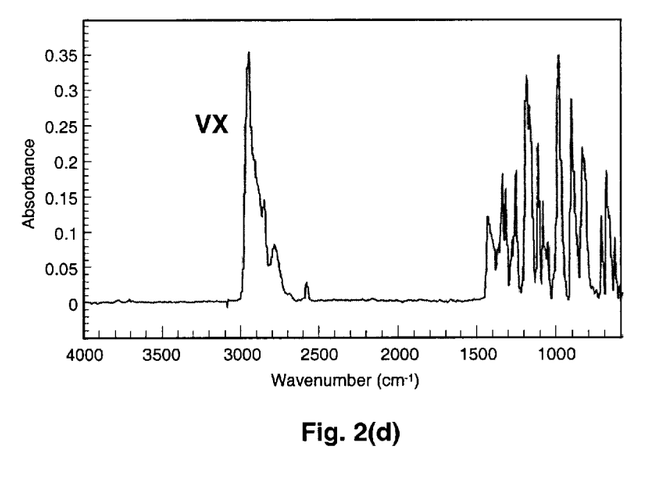

FIG. 1 is a plan view of a spectral sensing system 10, according to an embodiment of the present invention. The system 10 includes a radiation source 12, a telescope 14 and a spectrometer 16. The radiation source 12 can be any suitable laser or microwave source consistent with the discussion herein. The telescope 14 is a Newtonian type telescope, including a collecting mirror 18 for receiving radiation from a scene and a turning mirror 20. However, the telescope 14 can be any suitable telescope for receiving and focusing radiation from a scene consistent with the discussion herein. The spectrometer 16 can be any type of spectral detecting device that provides a spectral display over a predetermined spectrum, such as an FTIR spectrometer, an acousto-optic spectrometer, or a grating dispersed spectrometer. The source 12, telescope 14 and spectrometer 16 can be mounted within a suitable housing, and can be included on a platform capable for scanning over a wide area for increased surveillance. Additionally, the system 10 can be made compact and portable to be readily moved from place to place.

The radiation source 12 emits a radiation beam 22 towards a pair of turning mirrors 24 and 26 to align the beam 22 to be near co-linear with radiation received by the telescope 14 from the scene. The radiation beam 22 can be microwave, millimeter wave, infrared, visible or ultraviolet radiation, depending on the particular application and system being used, as will be discussed below. The radiation beam 22 is directed towards a suspected chemical cloud 28 to excite molecules within the cloud 28 to cause heat to be generated to increase the cloud's temperature relative to the background, usually sky, mountains or other terrain. In alternate embodiments, the radiation beam 22 can be directed towards the cloud 28 in a manner that is not co-linear with the emissions from the cloud 28. In this type of design, the location of the cloud 28 can also be determined as the intersection point between the radiation beam 22 and the field of view of the telescope 14.

The source 12 can be selected so that the wavelength of the radiation beam 22 is in resonance with a particular target molecule or molecules existing in the cloud being detected. The wavelength of the radiation beam 22 can also be selected to be in resonance with the absorption lines of water vapor or oxygen molecules commonly present in air. The resonance causes the target molecules, water vapor or oxygen molecules to rotate or vibrate which causes their energy to increase. Also, electrical transistions may occur in the molecules. The radiation energy absorbed by the water vapor, the oxygen molecules or the target molecules in the cloud 28 is thermalized due to collision energy transfer causing inter-molecular relaxation. At atmospheric pressure, this thermalization is very rapid. This collisional energy redistribution results in heating the molecules in the cloud 28. An increase in the temperature of the cloud 28 will increase the emission intensity of the molecules in the cloud against the background, resulting in an improved detection of the molecules. If the wavelength of the electromagnetic radiation is chosen to be in resonance with the absorption lines of the target molecules, the returned emission intensity, as a function of the excitation wavelength, can be used to provide an additional way for discrimination against possible interference background chemicals. This is because the returned emission intensity from the target molecules should increase substantially as the excitation is tuned to the resonance absorption lines of the target molecules. In the contrast, the emission intensity from background chemicals should not increase appreciably at these excitation wavelengths.

The telescope 14 collects thermal emission returned from the cloud 28. The spectral content of the emission is then analyzed by the spectrometer 16. The emission spectrum, typical in the 8–14 micron region, is used to identify the molecules in the cloud 28 by comparing the detected emissions to the known "fingerprint" vibrational spectrum of predetermined molecules. Alternatively, an imaging spectrometer, such as a hyperspectrometer imager, can be used to obtain spatially resolved spectrum. The contrast from the spatially resolved spectrum can further be used to discriminate against any other interference background chemicals that may be present.

Several electromagnetic radiation sources, including infrared lasers, such as a $CO_2$ laser and a DF laser, and microwaves may be used as the radiation source. The $CO_2$ laser is a preferred excitation source for detection of chemical agent cloud. This is because several phosphonate-type chemical agents, including sarin (GB), soman (GD), tabun (GA) and VX, as shown in FIG. 2, have absorption bands in the 9–10 $\mu$ region that can be excited by a $CO_2$ laser.

Figure 3:
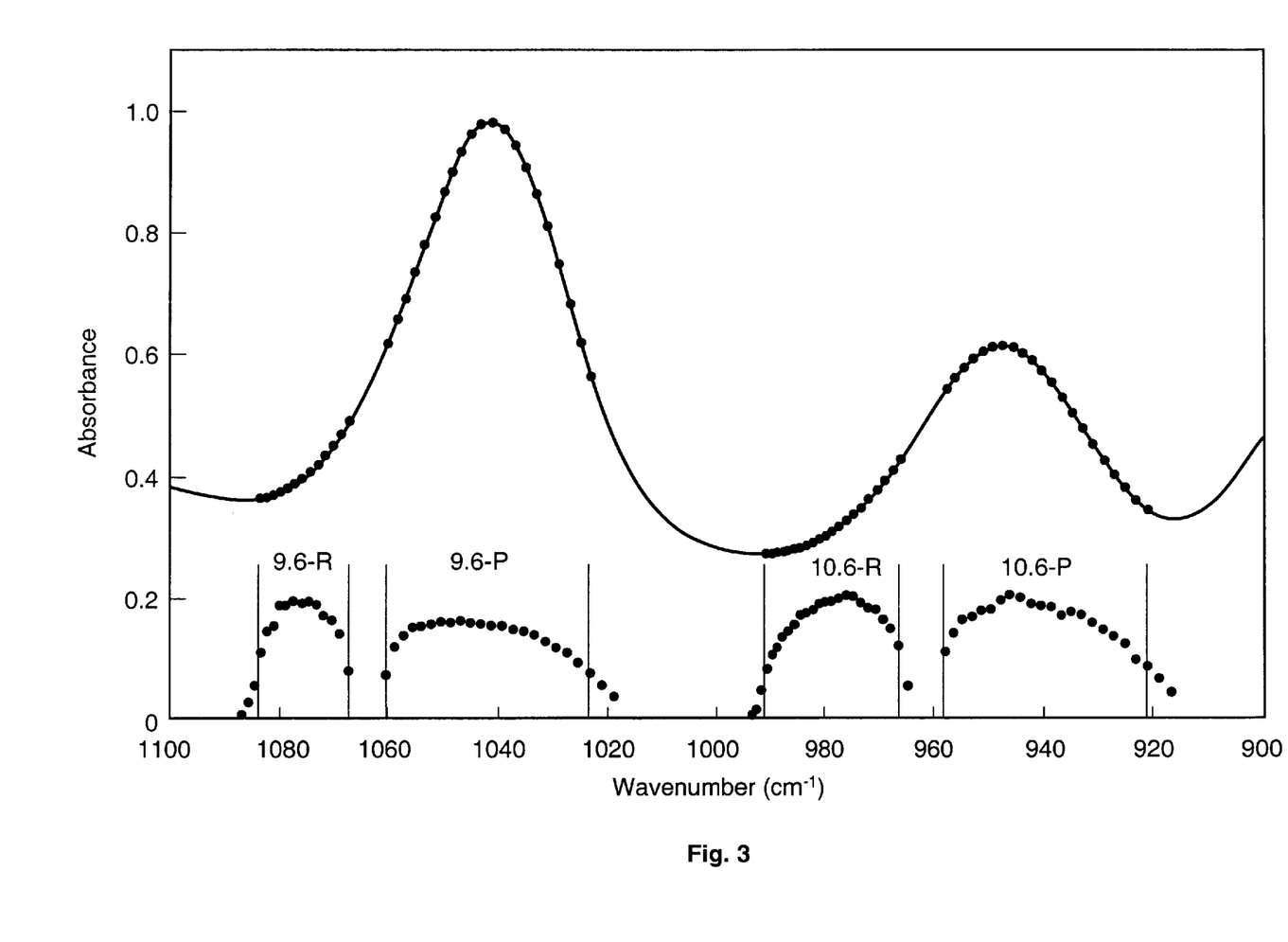

FIG. 3 illustrates some overlapping of $CO_2$ laser lines with the absorption spectrum of agent VX. The upper curve shows the absorption spectrum of agent VX and the dots on the curve show the overlapping of the absorption curve with relatively strong $^{12}CO_2$ laser lines. The lower curve shows the intensity distribution of a typical tuned $^{12}CO_2$ laser. The strong peaks of the VX vapor can be excited by the p-branch of the 9.6-$\mu$m band or 10.6-$\mu$m band of a $^{12}CO_2$ laser. A single strong $CO_2$ laser line that overlaps with the strong absorption band may be employed for initial searching of the target chemicals. Further identification of target molecules can be achieved by comparing the returned emission at different $CO_2$ laser lines against the "fingerprint" absorption spectrum of the target chemicals.

Figure 4:
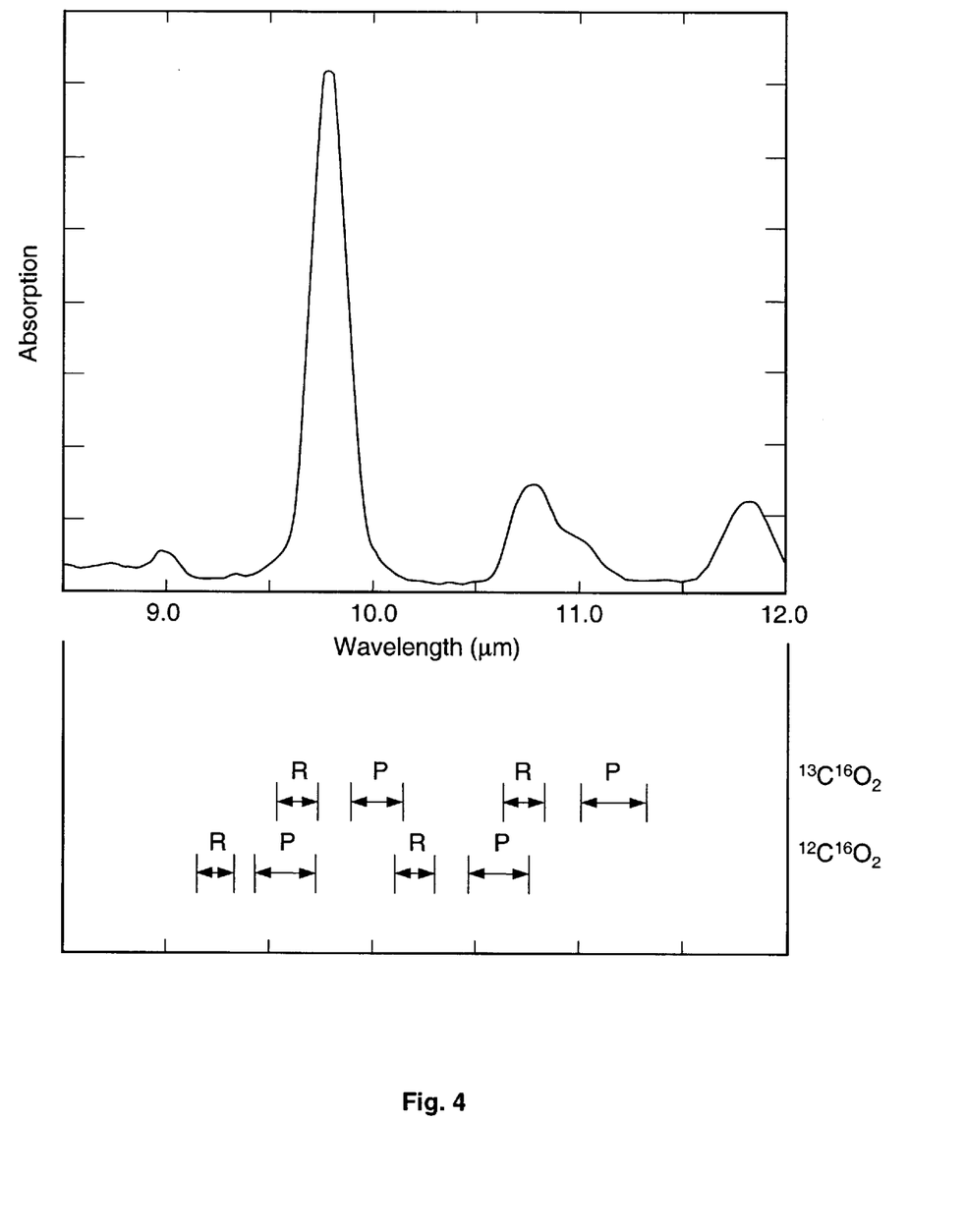
FIG. 4 is a graph with wavelength on the horizontal axis and absorption on the vertical axis showing absorption spectrum of sarin relative to a $CO_2$ laser tuning range.
Figure 5:
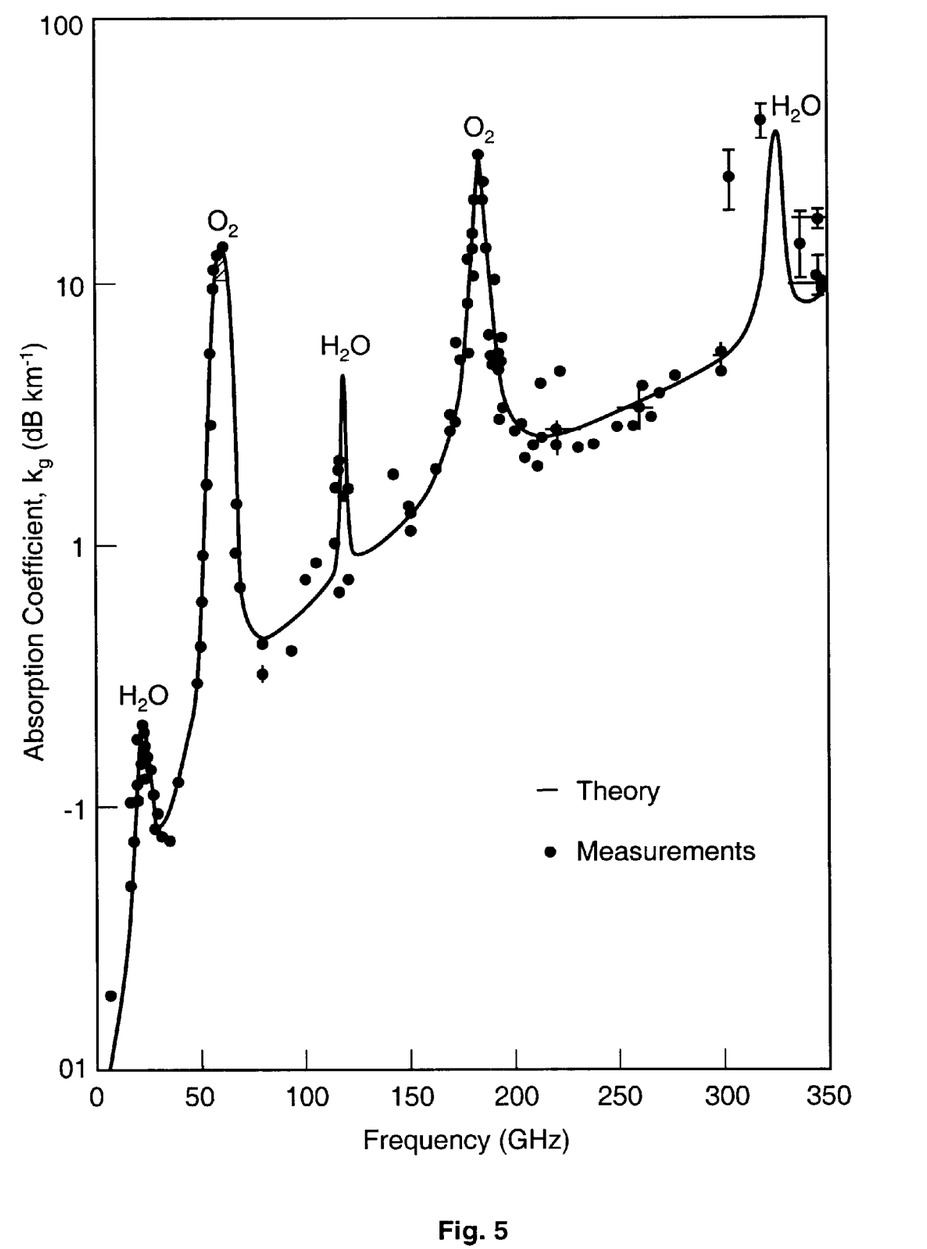
FIG. 5 is a graph with frequency on the horizontal axis and absorption coefficient on the vertical axis showing microwave absorption from atmospheric gases.

FIG. 4 shows another example of the overlapping of sarin (agent GB) with $CO_2$ laser, including both isotopes of $^{12}CO_2$ and $^{13}CO_2$. This illustrates that strong absorption bands of the chemicals can be excited by a different isotope of a $CO_2$ laser.

Table 1 shows an estimate of the power required for heating a GB vapor cloud by 10° C. This assumes that a $CO_2$ laser is tuned near the peak absorption of the vapor, the concentration of the GB is assumed to be about 100 ppm in the air, the laser beam on the target cloud is about 5-cm diameter, and the duration of irradiation is about 1 second. Table 1 shows the required $CO_2$ laser power is relatively low, about 28 W, mainly because of relatively strong absorption cross-sections of the phosphonate bands in the 9–10$\mu$ region. In addition, the range from the source to the target cloud can be quite long, exceeding more than 5 km, mainly because the air is practically transparent to the $CO_2$ laser in the range of concern.

The DF laser, as well some HF lasers, may also be used as an excitation source. As shown in FIG. 2, many of the chemical agents have absorption bands near the region that overlap with either the DF or HF laser lines. Table 1 shows that the required DF laser for heating a GB vapor cloud of 100 ppm in the air by 10° C. is relatively mild, about 137 W for a duration of 1 second. The estimate again assumes the laser beam on the target cloud is about 5-cm diameter.

When $CO_2$ lasers are used as an excitation source, strong scattered intensity from the $CO_2$ laser may interfere with the FTIR spectral measurements. It is desirable to turn on the laser for a certain duration and then turn off the laser momentary during the FTIR spectral measurements. Although the $CO_2$ laser is turned off momentary, the chemical cloud won't cool off immediately, as it takes some time to lose its heat to the surrounding air.

Microwave radiation may also be used to heat a chemical cloud. One convenient way is to heat the cloud via the excitation of the $O_2$ or $H_2O$ vapor that is present in the cloud. The energy absorbed by $O_2$ or $H_2O$ can be thermalized rapidly and heat the cloud. Hence, in this approach, a chemical cloud can be heated without prior knowledge of the constituents and their absorption spectra. FIG. 5 shows the absorption bands of $O_2$ or $H_2O$ in air from about 15 GHz to 350 GHz. A FTIR spectrometer can be used to identify the chemical constituents by spectral analyzing the returned radiation in the infrared region from about 8 to 14 $\mu$m. A microwave source in conjunction with a spectrometer is like providing an "universal detector" capable of detecting various kinds of chemical vapor. However, a relatively high power microwave may be needed since a substantial fraction of the power is absorbed by the $O_2$ or $H_2O$ vapor in transmission through the air before reaching the target.

An alternative way is to excite the chemicals directly by tuning the microwave frequency in resonance with the chemical absorption lines. The absorption coefficients for chemical warfare agents are generally not known too well. However, several of other molecules, such as $H_2S$, $SO_2$, and $CH_3I$ have been reported. See, for example, N. Gopalsami, S. Bakhtiari, A. C. Raptis, S. L. Dieckman, and DeLucia, "Millimeter-wave Measurements of Molecular Spectra with Application to Environmental Monitoring," IEEE Transactions on Instrumentation and Measurement, Vol. 45, p. 225–230, 1996.

Microwave or millimeter wave radiation has a very different spectral region than infrared radiation, which is the emissions range usually analyzed by the spectrometer 16. Therefore, minimal interference in the measurements from using microwave or millimeter wave radiation is expected. The spectral range of interest for analyzing the returned emissions is typically between 8–14 microns, where many chemical vapors, such as certain chemical agents, emit radiation.

Although the path between the cloud and the sensor unit is also heated, if the excitation via water vapor or oxygen absorption lines is chosen, the return emission is expected to have minimal absorption by the column of the heated air. This is because the absorption by air is quite weak in this spectral region of interest. Although there are weak $CO_2$ absorption bands in the 8–14 micron region due to the hot-band absorption from the $\mu_2$ and $2\mu_2$ levels of $CO_2$, these bands are normally fairly weak near ambient temperature. It is anticipated that these absorption bands will not cause any serious interference of the returned signal in the spectral range of 8 to 14 $\mu$m of interest, if the temperature rise is kept below 10 to 20° C.

The required microwave power for the source 12 depends upon the necessary temperature difference between the cloud 28 and the background, the range of the cloud 28, and the absorption coefficient and concentration of the absorber. Table 1 shows an estimate of the required microwave power and range for heating a 100-ppm GB vapor cloud by 10° C., via absorption of $O_2$ at about 60 GHz, $H_2O$ at 22.3 GHz, and GB vapor at 90 GHz, for a duration of 1 second. The absorption cross-section of $O_2$ and $H_2O$ are from Ulaby, et al. The absorption cross section for GB is taking to be an average value of that of $H_2S$, $SO_2$, and $CH_3I$ cited in the above reference by Gopalsami, et al. It is assumed that the beam 22 can be focused to a spot size of 5-cm diameter at a 200 meter range and 10-cm diameter at a 5-km range, and that the source 12 is on for 1 second.

There are trade-offs among choice of different absorbers. It appears that $O_2$ yields a relative low required power of about 16 kW mainly caused by relatively high absorption of $O_2$ in the air. However, the range is likely limited to 200 m. On the other hands, $H_2O$ yields a substantially high required energy of about 270 kW, although the range can exceed 5 km. GB vapor may not be a good choice of absorber because of exceedingly high required microwave power. Of course, the required microwave power can be substantially reduced if the irradiation can be extended over a longer duration.

TABLE 1

Required Laser of Microwave Power for Heating 100-ppm GB chemical Cloud by 10° for 1 second duration

| Excitation source | $CO_2$ laser | DF laser | Microwave | Microwave | Microwave |
|---|---|---|---|---|---|
| Wavelength | ~9.6 micron | ~3.58 micron | ~60 GHz | ~22.3 GHz | ~90 GHz |
| Absorbing medium | GB vapor cloud | GB vapor cloud | Oxygen | Watervapor(30% $H_2O$) | GB vapor cloud |
| Cross section, $cm^2$ | $3.4 \times 10^{-18}$ | $0.7 \times 10^{-18}$ | $4.9 \times 10^{-24}$ | $1.9 \times 10^{-24}$ | $1.0 \times 10^{-21}$ |
| Beam diameter | 5 cm | 5 cm | 5 cm | 10 cm | 10 cm |
| Range | 0–5 Km | 0–5 Km | 0–200 m | 0–5 Km | 0–5 Km |
| Required Power | 28 W | 137 W | 16 KW | 270 KW | 380 KW |

One article has investigated the relationship between improvements in detection sensitivity and the temperature difference between the target vapor cloud and the background temperature. See T. C. Gruber and J. Ditillo, "Quality assurance measurements for passive FTIR data collection," AAPCA Specialty Conference Proceedings SP Optical Remote Sensing for Environmental and Process Monitoring Proceedings of the 1995 Specialty Conference, Sep. 25–27, 1995. The quality in the returned emission spectrum was expressed as a "score". For temperatures closer to or below 2° C., the score is practically zero. Once the temperature passes a threshold value of ~2° C., the score increases markedly with increasing temperature difference. Hence, an increase in the temperature difference by 10° C. or higher, by means of the laser or microwave heating, provides an improvement in the sensitivity of detecting these molecules substantially.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A system for the detection and analysis of trace chemicals in an aggregate cloud, said system comprising:
   a radiation source, said radiation source directing a radiation beam towards the cloud, said radiation beam thermalizing the cloud to raise a bulk gas temperature of the cloud against its surrounding background;
   receiving optics for receiving emissions from the cloud as a result of the cloud having a higher temperature than the background; and
   a spectrometer responsive to the emissions from the receiving optics, said spectrometer generating a spectral display of certain constituents in the cloud.

2. The system according to claim 1 wherein the spectrometer is selected from the group consisting of FTIR spectrometers, acousto-optic spectrometers and grating dispersion spectrometers.

3. The system according to claim 1 wherein the receiving optics are part of a telescope.

4. A system for the detection and analysis of trace chemicals in an aggregate cloud, said system comprising:
   a radiation source, said radiation source directing a radiation beam towards the cloud, said radiation beam thermalizing the cloud to raise a bulk gas temperature of the cloud against its surrounding background, said radiation source generating a radiation beam selected from the group consisting of microwave, millimeter wave, infrared, visible, and ultraviolet radiation beams;
   receiving optics for receiving emissions from the cloud as a result of the cloud having a higher temperature than the background; and
   a spectrometer responsive to the emissions from the receiving optics, said spectrometer generating a spectral display of certain constituents in the cloud.

5. A system for the detection and analysis of trace chemicals in an aggregate cloud, said system comprising:
   a radiation source, said radiation source directing a radiation beam towards the cloud, said radiation beam thermalizing the cloud to raise a bulk gas temperature of the cloud against its surrounding background;
   receiving optics for receiving emissions from the cloud as a result of the cloud having a higher temperature than the background;
   directional optics positioned to receive the radiation beam from the radiation source and direct the radiation along a direction substantially co-linear with the direction of the emissions received from the cloud; and
   a spectrometer responsive to the emissions from the receiving optics, said spectrometer generating a spectral display of certain constituents in the cloud.

6. A system for the detection and analysis of trace chemicals in an aggregate cloud, said system comprising:
   a radiation source, said radiation source directing a radiation beam towards the cloud and generating a radiation beam having a wavelength that is in resonance with a particular target molecule existing in the cloud, said radiation beam thermalizing the cloud to raise a bulk gas temperature of the cloud against its surrounding background;
   receiving optics for receiving emissions from the cloud as a result of the cloud having a higher temperature than the background; and
   a spectrometer responsive to the emissions from the receiving optics, said spectrometer generating a spectral display of certain constituents in the cloud.

7. A system for the detection and analysis of trace chemicals in an aggregate cloud, said system comprising:
   a radiation source, said radiation source directing a radiation beam towards the cloud and generating a radiation beam having a wavelength that is in resonance with absorption lines of at least one of water vapor and oxygen molecules existing in the cloud, said radiation basin thermalizing the cloud to raise a bulk gas temperature of the cloud against its surrounding background;
   receiving optics for receiving emissions from the cloud as a result of the cloud having a higher temperature than the background; and
   a spectrometer responsive to the emissions from the receiving optics, said spectrometer generating a spectral display of certain constituents in the cloud.

8. A system for detecting a chemical agent in a chemical cloud against a sky background, said system comprising:
   a radiation source, said radiation source directing a radiation beam towards the cloud to thermalize and heat constituents in the cloud and raise its temperature relative to the temperature of the background, said increase in the temperature of the cloud enhancing passive emissions from the cloud:
   a telescope responsive to the emissions from the cloud as a result of the cloud having a higher temperature than the background, said telescope focusing and directing the emissions; and
   a spectrometer responsive to the emissions from the telescope, said spectrometer generating a spectral display of the constituents in the cloud.

9. The system according to claim 8 wherein the radiation source generates a radiation beam having a wavelength that is in resonance with absorption lines of at least one of water vapor and oxygen molecules existing in the cloud.

10. The system according to claim 8 wherein the radiation source generates a radiation beam selected from the group consisting of microwave, millimeter wave, infrared, visible, and ultraviolet radiation beams.

11. The system according to claim 8 wherein the spectrometer is selected from the group consisting of FTIR spectrometers, acousto-optic spectrometers and dispersion spectrometers.

12. A system for detecting a chemical agent in a chemical cloud against a sky background, said system comprising:

a radiation source generating a radiation beam having a wavelength that is in resonance with a particular target molecule existing in the cloud, said radiation source directing a radiation beam towards the cloud to thermalize and heat constituents in the cloud and raise its temperature relative to the temperature of the background, said increase in the temperature of the cloud enhancing passive emissions from the cloud;

a telescope responsive to the emissions from the cloud as a result of the cloud having a higher temperature than the background, said telescope focusing and directing the emissions; and a spectrometer responsive to the emissions from the telescope, said spectrometer generating a spectral display of the constituents in the cloud.

13. A system for detecting a chemical agent in a chemical cloud against a sky background, said system comprising:

a radiation source, said radiation source directing a radiation beam towards the cloud to thermalize the cloud and raise its temperature relative to the temperature of the background, said increase in the temperature of the cloud enhancing passive emissions from the cloud;

a telescope responsive to the emissions from the cloud as a result of the cloud having a higher temperature than the background, said telescope focusing and directing the emissions:

directional optics positioned to receive the radiation beam from the radiation source and direct the radiation along a direction substantially co-linear with the direction of the emissions received from the cloud; and a spectrometer responsive to the emissions from the telescope, said spectrometer generating a spectral display of the constituents in the cloud.

14. A method of detecting a chemical agent in a gas cloud against a background, said method comprising the steps of:

heating the gas cloud relative to the background by directing a beam of radiation towards the cloud to thermalize the cloud to raise a bulk gas temperature of the cloud against its surrounding background and increase emissions from the cloud;

receiving the emissions from the cloud as a result of the cloud having a higher temperature than the background: and generating a spectral display indicative of the constituents in the cloud.

15. The method according to claim 14 wherein the step of heating the cloud includes using a radiation beam having a wavelength that is in resonance with a particular target molecule existing in the cloud.

16. The method according to claim 14 wherein the step of heating the cloud includes using a radiation beam having a wavelength that is in resonance with absorption lines of at least one of water vapor and oxygen molecules existing in the cloud.

17. The method according to claim 14 wherein the step of directing the radiation beam includes directing the radiation beam to be co-linear with the direction of the emissions received from the cloud.

18. A method of detecting a chemical agent in a gas cloud against a background, said method comprising the steps of:

heating the gas cloud relative to the background by directing a beam of radiation having a wavelength predominantly from the group consisting of microwave, millimeterwave, infrared, visible, and ultraviolet wavelengths towards the cloud to excite constituents in the cloud to raise a bulk gas temperature of the cloud against its surrounding background and increase emissions from the cloud;

receiving the emissions from the cloud as a result of the cloud having a higher temperature than the background; and generating a spectral display indicative of the constituents in the cloud.

* * * * *